(12) United States Patent
Omoto et al.

(10) Patent No.: US 10,123,681 B2
(45) Date of Patent: Nov. 13, 2018

(54) ENDOSCOPE INSERTION SHAPE OBSERVATION APPARATUS HAVING A CONTROLLER TO DRIVE BENDING OF INSERTION PORTION OF ENDOSCOPE

(71) Applicant: OLYMPUS CORPORATION, Hachioji-shi, Tokyo (JP)

(72) Inventors: Keijiro Omoto, Hachioji (JP); Takashi Yamashita, Hachioji (JP); Kensuke Miyake, Hamura (JP); Kazuhiro Hata, Hachioji (JP); Fumiyuki Onoda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/352,967

(22) Filed: Nov. 16, 2016

(65) Prior Publication Data
US 2017/0055809 A1    Mar. 2, 2017

Related U.S. Application Data

(63) Continuation of application No. PCT/JP2015/077360, filed on Sep. 28, 2015.

(30) Foreign Application Priority Data

Oct. 22, 2014 (JP) .................................. 2014-215615

(51) Int. Cl.
*A61B 1/005* (2006.01)
*A61B 1/01* (2006.01)
(Continued)

(52) U.S. Cl.
CPC .............. *A61B 1/0052* (2013.01); *A61B 1/00* (2013.01); *A61B 1/00039* (2013.01);
(Continued)

(58) Field of Classification Search
CPC ....... A61B 1/0051; A61B 1/0052; A61B 1/00; A61B 1/00039; A61B 1/00045;
(Continued)

(56) References Cited

U.S. PATENT DOCUMENTS

| 5,483,261 A * | 1/1996 | Yasutake ............... G06F 3/0425 |
| | | 178/18.03 |
| 2004/0030219 A1 * | 2/2004 | Kim .................... A61B 1/00039 |
| | | 600/101 |

(Continued)

FOREIGN PATENT DOCUMENTS

| JP | 2005-305047 A | 11/2005 |
| JP | 2007-319622 A | 12/2007 |
| WO | 2010/150697 A1 | 12/2010 |

OTHER PUBLICATIONS

Dec. 22, 2015 Search Report issued in International Patent Application No. PCT/JP2015/077360.

(Continued)

*Primary Examiner* — John P Leubecker
(74) *Attorney, Agent, or Firm* — Oliff PLC (57) ABSTRACT

An endoscope insertion shape observation apparatus includes an endoscope, a magnetic field generation coil provided at an insertion portion of the endoscope and configured to generate a magnetic field, an antenna unit configured to receive a coil signal from the magnetic field generation coil, a bending portion configured to bend the insertion portion, a bending drive section configured to drive the bending portion to bend, an insertion shape processing circuit configured to generate an insertion shape of the endoscope inserted into a subject according to a signal received from the antenna unit, a touch panel configured to display a generation result of the insertion shape processing circuit and be able to perform touch operation, and a drive section control circuit configured to control a drive amount of the bending drive section based on the touch operation on a desired location of the insertion shape displayed on the touch panel.

10 Claims, 8 Drawing Sheets

(51) Int. Cl.
*A61B 1/00* (2006.01)
*G02B 23/24* (2006.01)
*H04N 5/225* (2006.01)

(52) U.S. Cl.
CPC ........ *A61B 1/00045* (2013.01); *A61B 1/0051* (2013.01); *A61B 1/00078* (2013.01); *G02B 23/2476* (2013.01); *H04N 5/2256* (2013.01); *H04N 2005/2255* (2013.01)

(58) Field of Classification Search
CPC . A61B 1/00006; A61B 1/00078; A61B 5/748; A61B 5/7435; A61B 5/062; A61B 2034/2051; G02B 23/2476; H04N 5/2256; H04N 2005/2255
USPC .......................................... 700/264; 600/144
See application file for complete search history.

(56) References Cited

U.S. PATENT DOCUMENTS

| | | | | |
|---|---|---|---|---|
| 2004/0049097 | A1* | 3/2004 | Miyake | A61B 1/00039 600/150 |
| 2006/0015012 | A1* | 1/2006 | Sato | A61B 1/00006 600/118 |
| 2007/0027361 | A1 | 2/2007 | Uchimura et al. | |
| 2007/0270649 | A1* | 11/2007 | Long | A61B 1/00078 600/144 |
| 2007/0270650 | A1* | 11/2007 | Eno | A61B 1/00045 600/145 |
| 2010/0069723 | A1* | 3/2010 | Islam | H01S 3/302 600/300 |
| 2010/0099951 | A1* | 4/2010 | Laby | A61B 1/0052 600/144 |
| 2010/0324370 | A1* | 12/2010 | Dohi | A61B 1/00078 600/144 |
| 2011/0208000 | A1 | 8/2011 | Honda et al. | |
| 2012/0173217 | A1* | 7/2012 | Heimbecher | G06F 19/3437 703/7 |
| 2013/0179820 | A1* | 7/2013 | Asami | A61B 1/00045 715/771 |
| 2016/0354166 | A1* | 12/2016 | Popovic | A61B 34/30 |

OTHER PUBLICATIONS

Aug. 16, 2016 Office Action issued in Japanese Patent Application No. 2016-526247.

* cited by examiner

FIG.8

ENDOSCOPE INSERTION SHAPE OBSERVATION APPARATUS HAVING A CONTROLLER TO DRIVE BENDING OF INSERTION PORTION OF ENDOSCOPE

CROSS REFERENCE TO RELATED APPLICATION

This application is a continuation application of PCT/JP2015/077360 filed on Sep. 28, 2015 and claims benefit of Japanese Application No. 2014-215615 filed in Japan on Oct. 22, 2014, the entire contents of which are incorporated herein by this reference.

BACKGROUND OF THE INVENTION

1. Field of the Invention

The present invention relates to an endoscope insertion shape observation apparatus, and more particularly, to an endoscope insertion shape observation apparatus configured to observe an insertion state of an endoscope.

2. Description of the Related Art

Conventionally, endoscopes for medical use are widely used which insert an elongated insertion portion into a bent body cavity to observe organs or the like in deep parts in the body cavity without dissecting the body surface or which use, if necessary, a treatment instrument inserted into a treatment instrument channel of an endoscope insertion portion, to realize various types of therapy or treatment or the like.

Since a lumen such as a large intestine or a small intestine in a body cavity which is a subject is bent, making it clear up to which position of the lumen, the endoscope insertion portion is inserted or what shape the endoscope insertion portion takes may improve operability of observation or treatment using the endoscope.

Thus, for example, Japanese Patent Application Laid-Open Publication No. 2005-305047 discloses an endoscope insertion shape observation apparatus configured to incorporate a shape detection coil in the endoscope insertion portion, detect the position of the shape detection coil by receiving an electromagnetic field signal generated by the shape detection coil and display the shape of the endoscope insertion portion on a monitor or the like.

Regarding the insertion of a large intestine endoscope into the large intestine which includes many complicated bent conduits, since the shape of the intestine is extremely varied from one person to another, the insertion of the large intestine endoscope involves difficult manipulation and mastering such manipulation takes considerable effort. For that reason, a method is adopted which uses an endoscope insertion shape observation apparatus as disclosed in Japanese Patent Application Laid-Open Publication No. 2005-305047 as auxiliary insertion means, determines a bending angle while watching the endoscope insertion shape and assuming the luminal direction from the endoscope position, takes advantage of varying rigidity depending on how the endoscope advances and inserts the endoscope into deep parts.

SUMMARY OF THE INVENTION

An endoscope insertion shape observation apparatus according to an aspect of the present invention includes an endoscope, a magnetic field generation coil provided at an insertion portion of the endoscope and configured to generate a magnetic field, an antenna unit configured to receive a coil signal from the magnetic field generation coil, a bending portion configured to bend the insertion portion, a bending drive section configured to drive the bending portion to bend, an insertion shape generation section configured to generate an insertion shape of the endoscope inserted into a subject according to a signal received from the antenna unit, a touch panel configured to display a generation result of the insertion shape generation section and be able to perform touch operation, and a control section configured to control a drive amount of the bending drive section based on the touch operation on a desired location of the insertion shape displayed on the touch panel.

Furthermore, an endoscope insertion shape observation apparatus according to another aspect of the present invention includes an endoscope, a magnetic field generation coil provided at an insertion portion of the endoscope and configured to generate a magnetic field, an antenna unit configured to receive a coil signal from the magnetic field generation coil, a rigidity varying section configured to vary rigidity of the insertion portion, a rigidity varying drive section configured to drive the rigidity varying section to vary rigidity, an insertion shape generation section configured to generate an insertion shape of the endoscope inserted into a subject according to a signal received from the antenna unit, a touch panel configured to display a generation result of the insertion shape generation section and be able to perform touch operation, and a control section configured to control a rigidity varying amount of the rigidity varying drive section based on the touch operation on a desired location of the insertion shape displayed on the touch panel.

DETAILED DESCRIPTION OF THE PREFERRED EMBODIMENT

Hereinafter, an embodiment of the present invention will be described with reference to the accompanying drawings.

Figure 1:
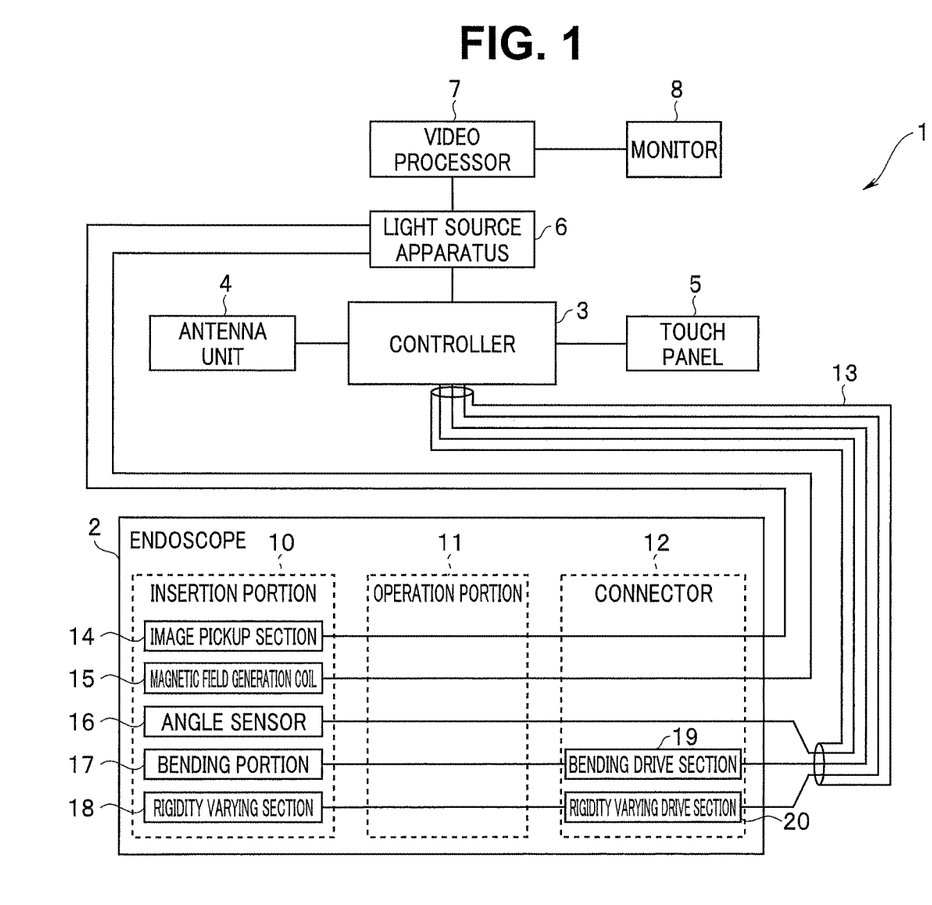
FIG. 1 is a block diagram illustrating an overall configuration of an endoscope insertion shape observation apparatus according to an embodiment.
Figure 2A:
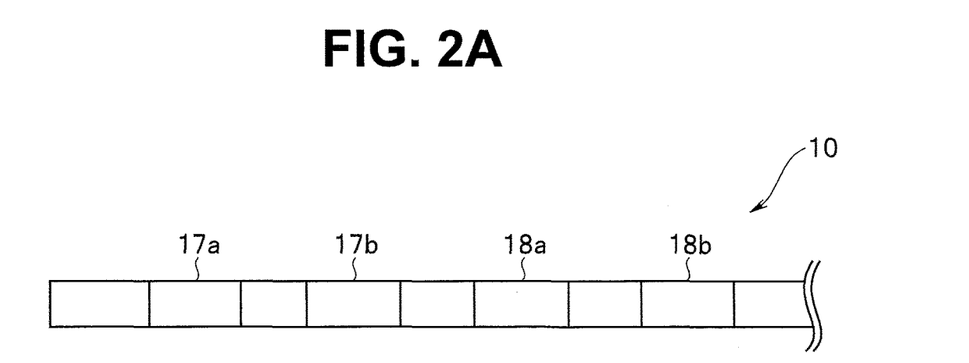
FIG. 2A is a diagram for describing an arrangement of a bending portion and a rigidity varying section in an insertion portion.
Figure 2B:
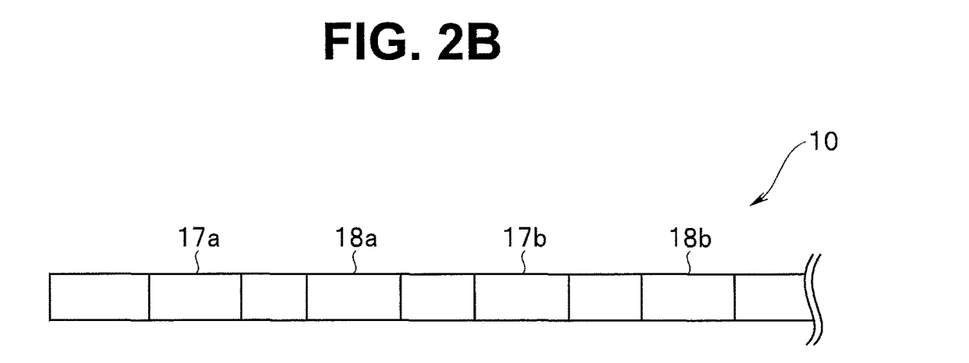
FIG. 2B is a diagram for describing an arrangement of the bending portion and the rigidity varying section in the insertion portion.
Figure 3:
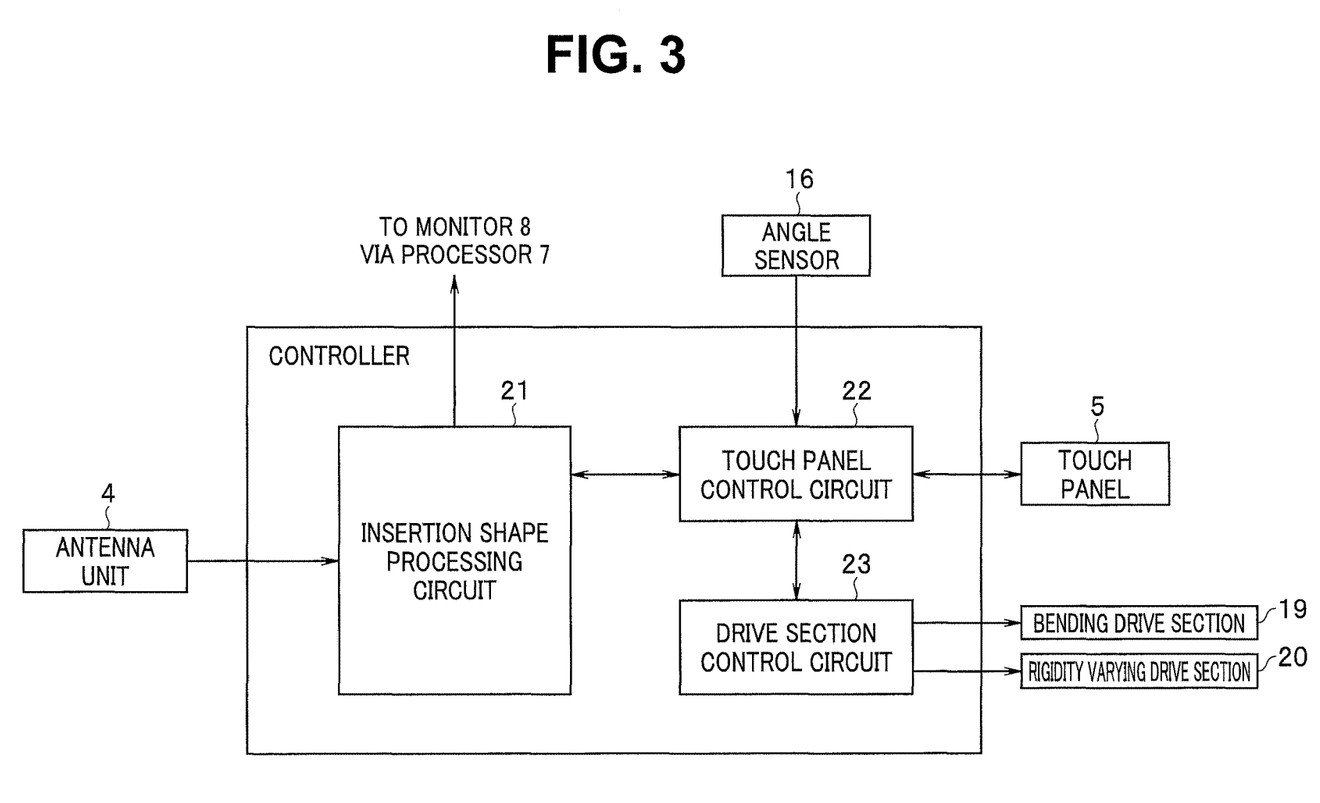
FIG. 3 is a block diagram for describing a detailed circuit configuration of a controller.

First, a configuration of an endoscope insertion shape observation apparatus according to an embodiment of the present invention will be described using FIG. 1 to FIG. 3. FIG. 1 is a block diagram illustrating an overall configuration of an endoscope insertion shape observation apparatus according to an embodiment, FIG. 2A and FIG. 2B are diagrams for describing an arrangement of a bending portion and a rigidity varying section in an insertion portion and FIG. 3 is a block diagram for describing a detailed circuit configuration of a controller.

The endoscope insertion shape observation apparatus 1 is constructed of an endoscope 2, a controller 3, an antenna unit 4, a touch panel 5, a light source apparatus 6, a video processor 7 and a monitor 8.

The endoscope 2 is constructed of an elongated insertion portion 10 inserted into a subject, an operation portion 11 provided on a proximal end side of the insertion portion 10, and a connector 12 provided on a proximal end side of the operation portion 11. Furthermore, a drive cable 13 extends from the connector 12 and the endoscope 2 is connected to the controller 3 via the drive cable 13.

The insertion portion 10 is constructed of an image pickup section 14 configured to pick up an image of an object, a magnetic field generation coil 15 configured to generate a magnetic field, an angle sensor 16 configured to detect an angle of the insertion portion 10, a bending portion 17 configured to bend the insertion portion 10, and a rigidity varying section 18 configured to vary rigidity of the insertion portion 10. The connector 12 is constructed of a bending drive section 19 configured to bend the bending portion 17 and a rigidity varying drive section 20 configured to vary rigidity of the rigidity varying section 18. The angle sensor 16, the bending drive section 19 and the rigidity varying drive section 20 are connected to the drive cable 13, and connected to the controller 3 via the drive cable 13.

In the present embodiment, the insertion portion 10 is constructed of at least one or more bending portions 17 and at least one or more rigidity varying sections 18. For example, as shown in FIG. 2A, the insertion portion 10 is provided with a first bending portion 17a, a second bending portion 17b, a first rigidity varying section 18a and a second rigidity varying section 18b from the distal end side. Note that the arrangement of the bending portion 17 and the rigidity varying section 18 is not limited to FIG. 2A, but, as shown in FIG. 2B, the first bending portion 17a, the first rigidity varying section 18a, the second bending portion 17b and the second rigidity varying section 18b may be arranged in that order from the distal end side.

The light source apparatus 6 emits illumination light for illuminating an object. The illumination light is guided up to a distal end of the insertion portion 10 via an illumination light guide or the like, which is not shown, to illuminate the object. The image pickup section 14 is configured to pick up an image of the object illuminated with the illumination light from the light source apparatus 6 and output an image pickup signal to the video processor 7 via the light source apparatus 6.

The video processor 7 outputs an image signal acquired by applying predetermined image processing to the inputted image pickup signal to the monitor 8. In this way, an endoscope image picked up by the endoscope 2 is displayed on the monitor 8.

The magnetic field generation coil 15 is provided in plurality at a predetermined interval in the longitudinal direction of the insertion portion 10 and configured to generate a magnetic field through application of a current from the light source apparatus 6, for example. The antenna unit 4 receives the magnetic field generated from the magnetic field generation coil 15 and outputs the magnetic field as a coil signal to the controller 3.

As shown in FIG. 3, the controller 3 is constructed of an insertion shape processing circuit 21, a touch panel control circuit 22 and a drive section control circuit 23.

A coil signal from the magnetic field generation coil 15 received by the antenna unit 4 is inputted to the insertion shape processing circuit 21. The insertion shape processing circuit 21 as an insertion shape generation section generates insertion shape information of the insertion portion 10 of the endoscope 2 inserted into the subject based on the coil signal from the antenna unit 4 and outputs the insertion shape information to the touch panel control circuit 22.

The touch panel control circuit 22 receives angle information of the insertion portion 10 from the angle sensor 16. The touch panel control circuit 22 detects a distal end direction of the insertion portion 10 based on the angle information from the angle sensor 16 and causes the touch panel 5 to display the insertion shape of the insertion portion 10 of the endoscope 2.

An operator such as a surgeon performs a predetermined touch operation on the insertion shape of the insertion portion 10 displayed on the touch panel 5, and can thereby change a bending amount of the bending portion 17 or a rigidity varying amount of the rigidity varying section 18. A touch operation signal on the touch panel 5 is inputted from the touch panel control circuit 22 to the drive section control circuit 23.

Based on the touch operation on the touch panel 5, the drive section control circuit 23 outputs a drive control signal to control the bending amount of the bending portion 17 or the rigidity varying amount of the rigidity varying section 18 to the bending drive section 19 or the rigidity varying drive section 20. The bending drive section 19 controls the bending amount of the bending portion 17 in accordance with the drive control signal from the drive section control circuit 23. The rigidity varying drive section 20 controls the rigidity varying amount of the rigidity varying section 18 in accordance with the drive control signal from the drive section control circuit 23.

Figure 4A:
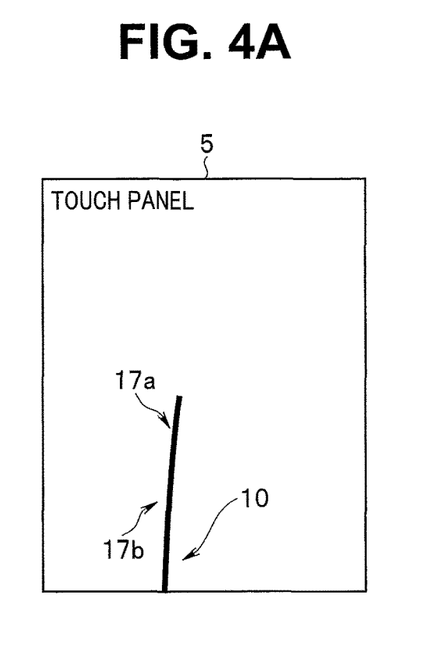
FIG. 4A is a diagram for describing an operation example of bending a first bending portion 17a on a touch panel 5.
Figure 4B:
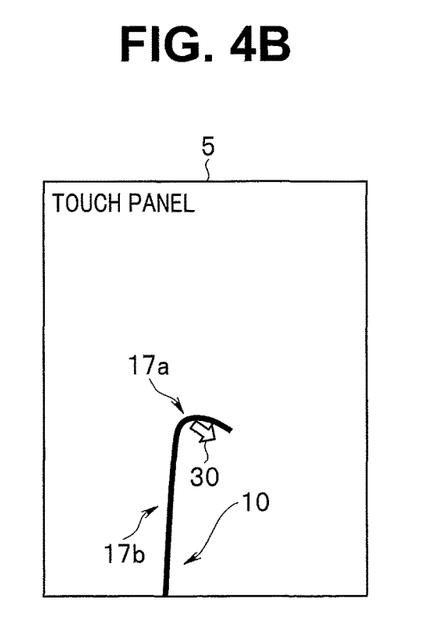
FIG. 4B is a diagram for describing an operation example of bending the first bending portion 17a on the touch panel 5.
Figure 4C:
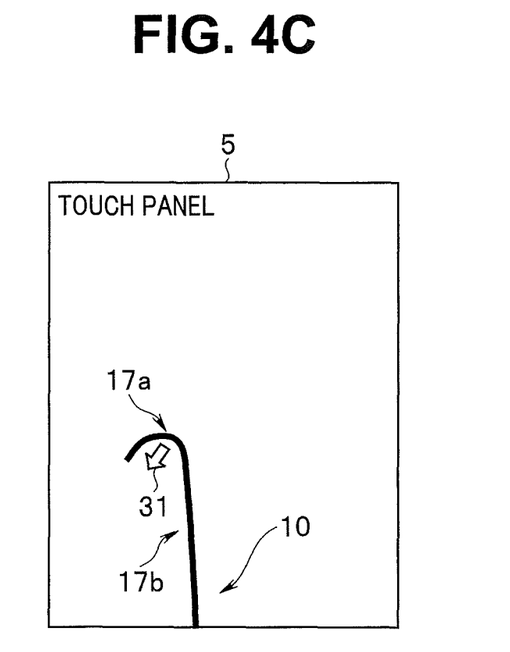
FIG. 4C is a diagram for describing an operation example of bending the first bending portion 17a on the touch panel 5.

Here, examples of bending operation and rigidity varying operation on the touch panel 5 will be described. FIG. 4A to FIG. 4C are diagrams for describing operation examples when bending the first bending portion 17a on the touch panel 5. Note that the insertion shape of the insertion portion 10 shown in FIG. 4A to FIG. 4C is a shape displayed on the touch panel 5 when the insertion portion 10 of the endoscope 2 is inserted during, for example, a large intestine inspection.

FIG. 4A illustrates an insertion initial state when the insertion portion 10 is inserted into the large intestine or the like, showing a state in which the distal end side of the insertion portion 10 of the endoscope 2 is not bent. In the insertion portion 10, the endoscope 2 including the first bending portion 17a and the second bending portion 17b shown in FIG. 2A is assumed. To allow the surgeon to perform bending operation on the touch panel, the touch panel control circuit 22 in the controller 3 processes angle information of the angle sensor 16 that detects the insertion portion shape and the direction of the distal end so that the bending operation can be performed on the insertion portion shape on the touch panel 5.

While observing an observation image displayed on the monitor 8 and the insertion shape of the insertion portion 10 on the touch panel 5, the surgeon selects a location of the bending portion 17 to be bent. The surgeon touches the region on the touch panel 5, moves the region toward an intended direction on the touch panel, and can thereby bend the insertion portion 10.

FIG. 4B illustrates a state in which the surgeon touches the first bending portion 17a on the insertion portion 10 on the touch panel 5 and operates the first bending portion 17a to move toward the lower right of the screen, that is, toward a direction denoted by an arrow 30. In this way, the first bending portion 17a is bent toward the lower right of the screen (direction denoted by the arrow 30).

On the other hand, FIG. 4C shows a state in which the surgeon touches the first bending portion 17a on the touch panel 5 and operates the first bending portion 17a toward a direction opposite to that in FIG. 4B, that is, toward the lower left of the screen (direction denoted by an arrow 31). In this way, the first bending portion 17a is bent toward the lower left of the screen. In this way, by bending the bending portion 17 through a touch operation on the touch panel 5, even an unexperienced surgeon can bend the bending portion 17 toward an intended direction.

Figure 5A:
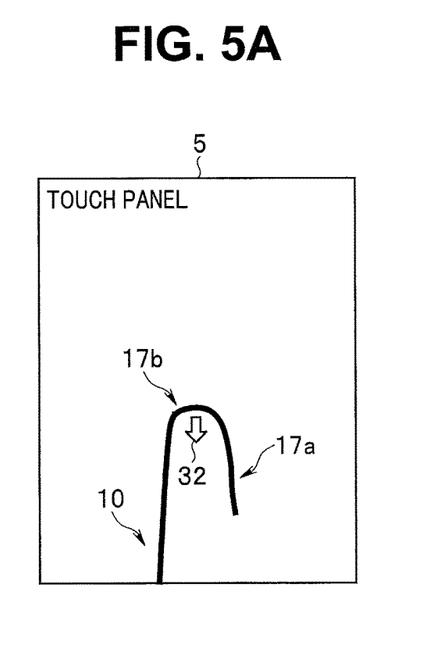
FIG. 5A is a diagram for describing an operation example of bending the first bending portion 17a and a second bending portion 17b on the touch panel 5.
Figure 5B:
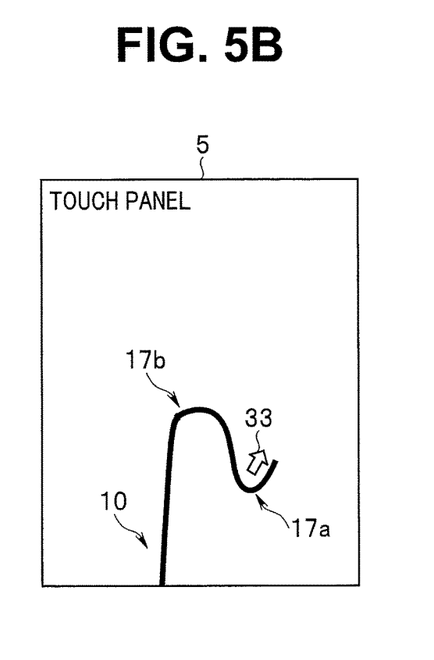
FIG. 5B is a diagram for describing an operation example of bending the first bending portion 17a and the second bending portion 17b on the touch panel 5.

FIG. 5A and FIG. 5B are diagrams for describing examples of bending operation on the first bending portion 17a and the second bending portion 17b on the touch panel 5.

The surgeon touches the second bending portion 17b on the touch panel 5 as shown in FIG. 5A and moves the second bending portion 17b toward an intended direction in which it is to be bent (direction denoted by an arrow 32). In this way, the second bending portion 17b is bent downward on the screen (direction denoted by the arrow 32).

The surgeon then touches the first bending portion 17a as shown in FIG. 5B and moves the first bending portion 17a toward an intended direction in which it is to be bent (direction denoted by arrow 33) on the touch panel. In this way, the first bending portion 17a is bent toward the upper right of the screen (direction denoted by the arrow 33). Thus, the surgeon performs touch operation on the first bending portion 17a and the second bending portion 17b while observing the insertion shape on the touch panel 5, and can thereby perform the bending operation toward the intended direction.

Figure 6:
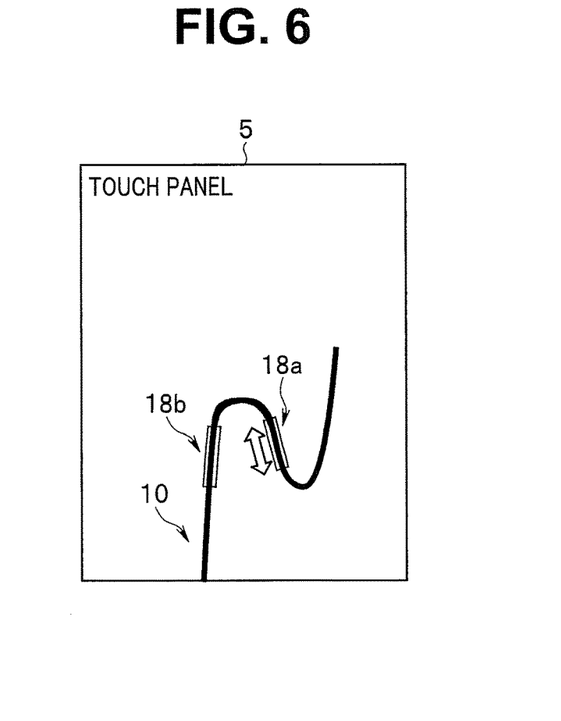
FIG. 6 is a diagram for describing an operation example of varying rigidity of a first rigidity varying section 18a and a second rigidity varying section 18b on the touch panel.

FIG. 6 is a diagram for describing an operation example when performing a rigidity varying operation on the first rigidity varying section 18a and the second rigidity varying section 18b on the touch panel.

The surgeon observes an insertion screen displayed on the monitor 8 and uses the rigidity varying according to a situation in which the distal end of the insertion portion 10 advances. According to the insertion shape on the touch panel 5, the surgeon traces a portion of the insertion portion 10 whose rigidity is desired to be increased on the touch panel 5.

For example, when the surgeon wants to increase the rigidity of the first rigidity varying section 18a, the surgeon traces a location of the first rigidity varying section 18a according to the insertion shape on the touch panel 5, and can thereby increase the rigidity of the first rigidity varying section 18a.

To further increase the rigidity of the first rigidity varying section 18a, the surgeon strongly pushes the first rigidity varying section 18a on the touch panel 5 or pushes it repeatedly, and can thereby further increase the rigidity of the first rigidity varying section 18a. The surgeon can also change the rigidity of the second rigidity varying section 18b as in the case of the first rigidity varying section 18a through touch operation on the touch panel 5.

Figure 7:
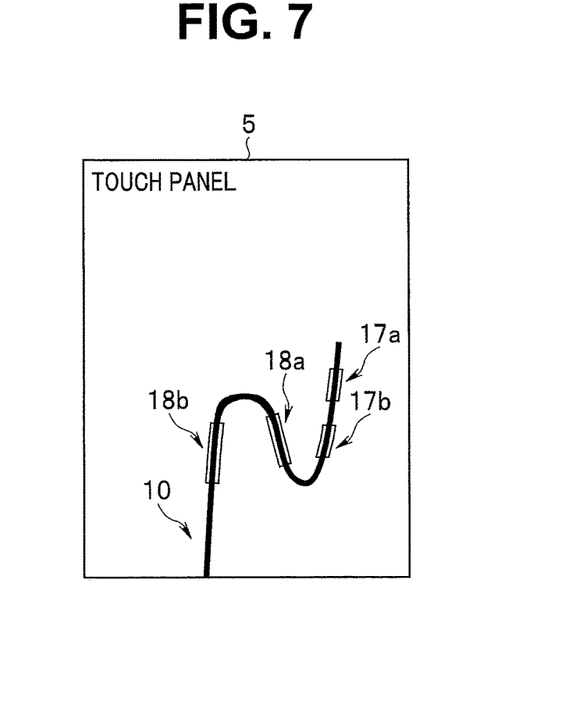
FIG. 7 is a diagram in which the bending portion 17 and the rigidity varying section 18 of the insertion portion 10 on the touch panel 5 are distinguished.

FIG. 7 is a diagram in which the bending portion 17 and the rigidity varying section 18 of the insertion portion 10 on the touch panel 5 are distinguished.

The insertion shape processing circuit 21 of the controller 3 generates insertion shape information which distinguishes the bending portion 17 and the rigidity varying section 18 by using different colors according to their respective positions. The insertion shape processing circuit 21 uses the same color for the first bending portion 17a and the second bending portion 17b, uses the same color for the first rigidity varying section 18a and the second rigidity varying section 18b, and uses different colors for the first bending portion 17a and the second bending portion 17b to distinguish those portions. Note that the insertion shape processing circuit 21 may also distinguish the first bending portion 17a, the second bending portion 17b, the first rigidity varying section 18a and the second rigidity varying section 18b by using different colors.

The surgeon identifies the bending portion 17 and the rigidity varying section 18 according to the colors on the insertion shape on the touch panel 5, and can thereby intuitively select an intended function, that is, the bending operation and the rigidity varying operation.

Thus, the endoscope insertion shape observation apparatus 1 performs predetermined touch operation on the bending portion 17 and/or the rigidity varying section 18 on the touch panel 5 while observing the insertion shape of the insertion portion 10 on the touch panel 5, and can thereby perform bending operation and/or rigidity varying operation. This allows anyone to simply perform bending operation and/or rigidity varying operation regardless of skill or experience of the surgeon.

Moreover, since the surgeon can intuitively perform bending operation toward an intended direction and/or intuitively perform rigidity varying operation, loss in the insertion time of the insertion portion 10 can be reduced and the burden on a patient during a large intestine inspection or the like can be reduced. Furthermore, since it is possible to simply perform bending operation toward a direction intended by the surgeon and/or simply perform rigidity varying operation, the surgeon can concentrate on the observation without being distracted by the endoscope operation and avoid overlooking of a lesion or the like.

Thus, according to the endoscope insertion shape observation apparatus of the present embodiment, any operator can intuitively operate the insertion portion while recognizing the endoscope insertion shape.

(Modification)

Figure 8:
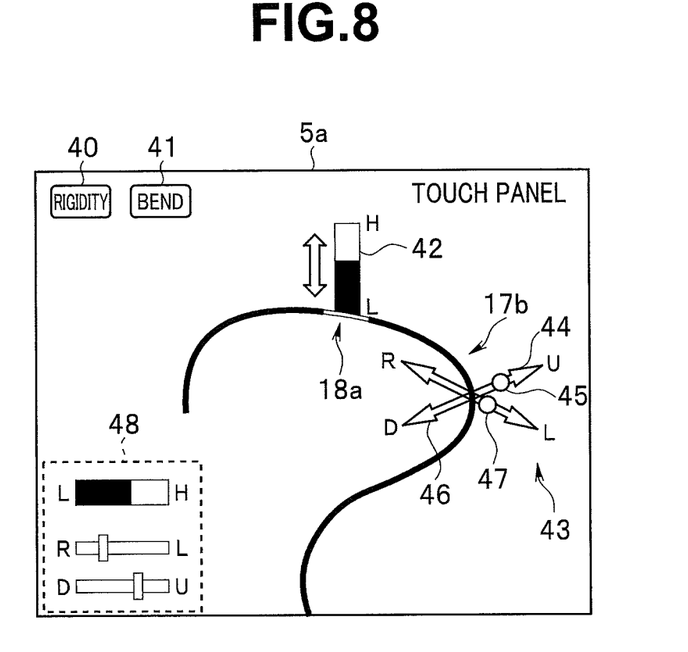
FIG. 8 is a diagram for describing another example of bending operation and rigidity varying operation on the touch panel.

Next, a modification will be described. The modification will describe another operation example of bending operation and rigidity varying operation on the touch panel. FIG. 8 is a diagram for describing another operation example of bending operation and rigidity varying operation on the touch panel.

The example in FIG. 8 assumes the insertion portion 10 in which the second bending portion 17b is disposed at a rear end of the first rigidity varying section 18a as shown in FIG. 2B. Note that the example in FIG. 8 only illustrates the first rigidity varying section 18a and the second bending portion 17b, whereas displays similar to those of the first rigidity varying section 18a and the second bending portion 17b are also possible for the first bending portion 17a and the second rigidity varying section 18b.

As shown in FIG. 8, the touch panel 5a includes a rigidity button 40 and a bending button 41. A rigidity level display section 42 is disposed at the first rigidity varying section 18a on the insertion shape of the insertion portion 10 displayed on a touch panel 5a and a bending amount display section 43 is disposed at the second bending portion 17b on the insertion shape of the insertion portion 10.

The bending amount display section 43 is constructed of an arrow 44 indicating an up/down direction (UD direction), a marker 45 to change the bending amount in the UD direction, an arrow 46 indicating a right/left direction (RL direction) and a marker 47 to change the bending amount in the RL direction. The arrow 44 indicating the UD direction and the arrow 46 indicating the RL direction are generated by the touch panel control circuit 22 based on a signal from the angle sensor 16 configured to detect a twisting direction of the insertion portion 10.

First, to vary the rigidity of the first rigidity varying section 18a, the surgeon presses the rigidity button 40 to enable a rigidity varying operation. The surgeon then touches the rigidity level display section 42 by a finger or the like, moves it in the up/down direction in the example in FIG. 8 and changes the rigidity of the first rigidity varying section 18a.

Such a touch operation signal is inputted from the touch panel control circuit 22 in the controller 3 to the drive section control circuit 23 as in the case of the aforementioned embodiment and supplied to the rigidity varying drive section 20 as a drive control signal.

To change the bending amount of the second bending portion 17b, the surgeon presses the bending button 41 to enable an operation on the bending amount. The surgeon then touches a marker 45 of the bending amount display section 43 by a finger or the like, moves the marker 45 along the arrow 44 and changes the bending amount of the second bending portion 17b in the UD direction. Similarly, the surgeon touches the marker 47 of the bending amount display section 43 by a finger or the like, moves the marker 47 along the arrow 46 and changes the bending amount of the second bending portion 17b in the RL direction.

Such a touch operation signal is inputted from the touch panel control circuit 22 in the controller 3 to the drive section control circuit 23 and supplied to the bending drive section 19 as a drive control signal.

Note that the example in FIG. 8 shows a configuration in which the rigidity level display section 42 and the bending amount display section 43 are provided on the insertion shape on the touch panel 5a, but without being limited to this, a configuration in which the rigidity level display section 42 and the bending amount display section 43 are provided on locations other than those on the insertion shape as a rigidity/bending amount operation bar 48.

Thus, the touch panel 5a is provided with the rigidity level display section 42 and the bending amount display section 43 and the rigidity and the bending amount can be operated through touch operation on the touch panel 5a, thus allowing the surgeon to perform intuitive rigidity varying operation and bending operation as in the case of the aforementioned embodiment.

The present invention is not limited to the aforementioned embodiment, but various modifications or alterations or the like can be made without departing from the spirit and scope of the present invention.

What is claimed is:

1. An endoscope insertion shape observation apparatus comprising:
    an endoscope including an insertion portion that defines a bending portion;
    a magnetic field generation coil provided at the insertion portion of the endoscope and configured to generate a magnetic field;
    an angle sensor configured to detect an angle of the insertion portion;
    an antenna configured to receive a coil signal from the magnetic field generation coil;
    a controller comprising:
        an insertion shape processing circuit configured to generate insertion shape information of the endoscope inserted into a subject according to a signal received from the antenna; and
        a touch panel control circuit configured to generate an insertion shape of the endoscope based on information on the angle of the insertion portion detected by the angle sensor and the insertion shape information generated by the insertion shape processing circuit;
    a touch panel configured to display the insertion shape generated by the touch panel control circuit and be able to perform touch operation; and
    the controller further comprising a drive section control circuit configured to control a bending amount of the bending portion based on the touch operation on a desired location of the insertion shape displayed on the touch panel.

2. The endoscope insertion shape observation apparatus according to claim 1,
    wherein the insertion portion comprises a plurality of bending portions, and
    the drive section control circuit, based on the touch operation on the touch panel, controls a bending amount of the plurality of bending portions.

3. The endoscope insertion shape observation apparatus according to claim 1,
    wherein the drive section control circuit controls the bending amount of the bending portion of the insertion portion, when touch operation is applied to a marker provided in a bending direction display area that displays a bending direction of the bending portion, based on a detection result of the angle sensor.

4. The endoscope insertion shape observation apparatus according to claim 3,
    wherein the bending direction display area is disposed in the bending portion of the insertion portion displayed on the touch panel, and
    the drive section control circuit changes the bending amount of the bending portion by applying touch operation to the marker provided in the bending direction display area disposed in the bending portion of the insertion portion and moving the marker along the bending direction display area.

5. The endoscope insertion shape observation apparatus according to claim 1, wherein the drive section control circuit controls, based on the touch operation, the bending amount of the insertion portion displayed on the touch panel.

6. An endoscope insertion shape observation apparatus comprising:
    an endoscope configured to vary a rigidity of an insertion portion;
    a magnetic field generation coil provided at the insertion portion of the endoscope and configured to generate a magnetic field;

an angle sensor configured to detect an angle of the insertion portion;

an antenna configured to receive a coil signal from the magnetic field generation coil;

a controller comprising:
- an insertion shape processing circuit configured to generate insertion shape information of the endoscope inserted into a subject according to a signal received from the antenna; and
- a touch panel control circuit configured to generate an insertion shape of the endoscope based on information on the angle of the insertion portion detected by the angle sensor and the insertion shape information generated by the insertion shape processing circuit; and a touch panel configured to display the insertion shape generated by the touch panel control circuit and be able to perform touch operation;

the controller further comprising a drive section control circuit configured to control a rigidity varying amount of a rigidity varying area of the insertion portion based on the touch operation on a desired location of the insertion shape displayed on the touch panel.

7. The endoscope insertion shape observation apparatus according to claim 6, wherein:
the drive section control circuit, based on the touch operation on the touch panel, controls a rigidity varying amount of a plurality of rigidity varying areas of the insertion portion.

8. The endoscope insertion shape observation apparatus according to claim 6,
wherein the drive section control circuit controls the rigidity varying amount of the rigidity varying area of the insertion portion when a touch operation is applied to a rigidity varying amount level display indicator on the touch panel.

9. The endoscope insertion shape observation apparatus according to claim 8, wherein the rigidity varying amount level display indicator is displayed on the touch panel, and
the drive section control circuit changes the rigidity varying amount by applying a touch operation to the rigidity varying amount level display indicator disposed in the rigidity varying area of the insertion portion and moving the rigidity varying amount level display indicator in a predetermined direction.

10. The endoscope insertion shape observation apparatus according to claim 6, wherein the drive section control circuit controls the rigidity varying amount based on the touch operation on the rigidity varying area of the insertion portion displayed on the touch panel.

* * * * *